US008073516B2

(12) United States Patent
Scharf et al.

(10) Patent No.: US 8,073,516 B2
(45) Date of Patent: *Dec. 6, 2011

(54) SEPARATING MOTION FROM CARDIAC SIGNALS USING SECOND ORDER DERIVATIVE OF THE PHOTO-PLETHYSMOGRAM AND FAST FOURIER TRANSFORMS

(75) Inventors: John E. Scharf, Oldsmar, FL (US); Bhavin B. Shah, Pune (IN)

(73) Assignee: Dolphin Medical, Inc., Hawthorne, CA (US)

( * ) Notice: Subject to any disclaimer, the term of this patent is extended or adjusted under 35 U.S.C. 154(b) by 1427 days.

This patent is subject to a terminal disclaimer.

(21) Appl. No.: 11/343,914

(22) Filed: Jan. 30, 2006

(65) Prior Publication Data

US 2006/0211930 A1  Sep. 21, 2006

(51) Int. Cl.
*A61B 5/1455* (2006.01)
(52) U.S. Cl. .................................................. 600/336
(58) Field of Classification Search .................. 600/310, 600/322, 323, 330, 336, 481, 500
See application file for complete search history.

(56) References Cited

U.S. PATENT DOCUMENTS

| | | | |
|---|---|---|---|
| 4,379,460 A | 4/1983 | Judell | |
| 4,800,495 A | 1/1989 | Smith | |
| 4,870,973 A | 10/1989 | Ueno | |
| 4,960,126 A | 10/1990 | Conlon et al. | |
| 4,974,597 A | 12/1990 | Walloch | |
| 4,994,965 A | 2/1991 | Crawford et al. | |
| 5,035,244 A | 7/1991 | Stokar | |
| 5,107,849 A | 4/1992 | Bellin et al. | |
| 5,170,794 A | 12/1992 | Reiche | |
| 5,308,982 A | 5/1994 | Ivaldi et al. | |
| 5,361,758 A | 11/1994 | Hall et al. | |
| 5,377,674 A | 1/1995 | Kuestner | |
| 5,503,160 A | 4/1996 | Pering et al. | |
| 5,542,428 A | 8/1996 | Jayne | |
| 5,575,284 A | 11/1996 | Athan et al. | |
| 5,603,321 A | 2/1997 | Kynor et al. | |
| 5,632,272 A | 5/1997 | Diab et al. | |
| 5,879,294 A | 3/1999 | Anderson et al. | |
| 5,971,930 A | 10/1999 | Elghazzawi | |
| 6,002,952 A | 12/1999 | Diab et al. | |
| 6,036,642 A | 3/2000 | Diab et al. | |
| 6,094,592 A | 7/2000 | Yorkey et al. | |
| 6,148,229 A | 11/2000 | Morris, Sr. et al. | |

(Continued)

*Primary Examiner* — Eric Winakur
(74) *Attorney, Agent, or Firm* — Novel IP

(57) ABSTRACT

The present invention is directed toward a pulse oximetry system for the determination of a physiological parameter capable of removing motion artifacts from physiological signals comprises a hardware subsystem and a software subsystem. The software subsystem is used in conjunction with the hardware subsystem to perform a method for removing a plurality of motion artifacts from the photo-plethysmographic data and for obtaining a measure of at least one physiological parameter from the data. The method comprises acquiring the raw photo-plethysmographic data, transforming the data into the frequency domain, analyzing the transformed data to locate a series of candidate cardiac spectral peaks (primary plus harmonics), reconstructing a photo-plethysmographic signal in the time domain with only the candidate cardiac spectral peaks (primary plus harmonics), computing the second order derivative of the reconstructed photo-plethysmographic signal, analyzing the candidate second order derivative photo-plethysmographic signal to determine the absence or presence of cardiac physiologic signal characteristics, and finally selecting the best physiologic candidate from the series of potential cardiac spectral peaks (primary plus harmonics) based upon a second derivative scoring system. This scoring system is preferentially based upon second derivative processing analysis, but can be equally applied using the first, third, fourth or other similar derivative processing analysis.

14 Claims, 11 Drawing Sheets

U.S. PATENT DOCUMENTS

| | | |
|---|---|---|
| 6,236,705 B1 | 5/2001 | Stergiopoulos et al. |
| 6,393,311 B1 | 5/2002 | Edgar, Jr. et al. |
| 6,405,076 B1 | 6/2002 | Taylor et al. |
| 6,473,632 B1 | 10/2002 | Myers |
| 6,650,918 B2 | 11/2003 | Terry |
| 7,020,507 B2 * | 3/2006 | Scharf et al. .................. 600/336 |

* cited by examiner

SEPARATING MOTION FROM CARDIAC SIGNALS USING SECOND ORDER DERIVATIVE OF THE PHOTO-PLETHYSMOGRAM AND FAST FOURIER TRANSFORMS

CROSS-REFERENCE TO RELATED APPLICATIONS

This application claims the benefit of U.S. Provisional Application No. 60/354,601, filed Jan. 31, 2002, entitled "Separating Motion from Cardiac Signals Using Second Order Derivative of the Photo-plethysmogram and Fast Fourier Transforms".

FIELD OF THE INVENTION

The present invention relates generally to correcting physiological signals, and more specifically to methods and systems for separation of artifacts, generated by undesirable motion, from physiological signals.

BACKGROUND OF THE INVENTION

Pulse oximeters are devices used to measure oxygen saturation level ($SpO_2$) in the blood. Conventional pulse oximeters perform photoplethysmography (PPG) to measure $SpO_2$. Photoplethysmography (PPG) is the electro-optic technique of measuring the cardiovascular pulse wave found throughout the human body. This pulse wave is caused by the periodic pulsations of arterial blood volume and is measured by the changing optical absorption. The measurement system consists of a light source, a photo-detector, a signal recovery, a processor, and a display system. These PPG devices differentiate between light absorption due to blood volume and that of other fluid and tissue constituents by observation that arterial blood flow pulsates while tissue absorption remains static. The PPG device measurements are non-invasive and can be applied to blood bearing tissue to conduct heart and respiration rate monitoring, to perform blood pressure studies, and to determine blood hemoglobin oxygen saturation.

Existing PPG devices have substantial disadvantages, however. The PPG device measurements are sensitive to corruption from external dynamics, causing motion artifacts that degrade the signal-to-noise ratio. An artifact may include unwanted signals superimposed onto the PPG signal, which can be induced by any external dynamics. For example, variation in the optical coupling between the probe head and the patient, possibly induced by patient movement, may cause an artifact. Motion artifacts can render it substantially difficult for the oximeter to accurately determine the patient's PPG signal, therefore causing errors in the pulse rate and oxygen saturation outputs.

Another limitation is that PPG relies on AC photo-plethysmogram (PPG) component, which is synchronous with cardiac pulsations but very small compared to the overall DC component, to determine $SpO_2$. Because the AC component is small relative to the DC component, accurate measurement of the AC component is difficult. Inaccuracies in AC component measurements cause inaccuracies in SpO2 measurements because oximeters compute $SpO_2$ using the relative magnitudes of the AC components of the different optical photo-plethysmograms. In addition, in poorly perfused patients, the circulation may not adequately modulate the light beams to the point where it is difficult to distinguish the synchronous cardiac pulsations from system noise. Thus, the usefulness of most commercial pulse oximeters is limited to situations in which patient is well perfused and subject to minimal motion.

Many pulse oximeters utilize time-domain algorithms that determine the period and amplitude of the photo-plethysmograms. These techniques typically analyze time-domain parameters such as slope transition, minima, maxima, and rise and fall time. Additionally, such algorithms may employ decision rules in order to reject data, which falls outside of certain limits.

A difficulty with these time-domain algorithms is that the $SpO_2$ is conventionally averaged with several recent values in order to reduce the disruptive effect of corrupted data. Such averaging is only useful if the number of bad values is small relative to the number of good data values.

Several advanced technology pulse oximeters have been introduced that utilize digital signal processing in the frequency domain as a solution to some scenarios presented by the cases where artifacts are induced.

An existing technique utilizes saturation-based digital signal processing algorithms. The patent is directed toward a signal processor which acquires a first signal, including a first desired signal portion and a first undesired signal portion, and a second signal, including a second desired signal portion and a second undesired signal portion, wherein the first and second desired signal portions are correlated. The signals may be acquired by propagating energy through a medium and measuring an attenuated signal after transmission or reflection. Alternatively, the signals may be acquired by measuring energy generated by the medium. A processor generates a noise reference signal which is a combination of only the undesired signal portions and is correlated to both the first and second undesired signal portions. The noise reference signal is then used to remove the undesired portion of each of the first and second measured signals via an adaptive noise canceller, preferably of the joint process estimator type. The processor may be employed in conjunction with an adaptive noise canceller in physiological monitors wherein the know properties of energy attenuation through a medium are used to determine physiological characteristics of the medium.

An underlying assumption in the '642 patent is that all motion artifacts come from the movement of lower-saturation venous blood. Furthermore, this motion artifact results in correlated red and infrared signals. A limitation with this algorithm is that when red and infrared signals become corrupted by sources other than moving arterial and venous blood, such as sensor movement relative to skin, the artifact can result in uncorrelated red and infrared signals. Thus this method has the potential to pick and choose for display a false high saturation created by non-venous artifact.

An existing technique involving a frequency domain approach utilizes a cardiac-based digital filtering algorithm. This Kalman filtering algorithm minimizes chaotic random signal artifact, regardless of the red and infrared correlation. One drawback of this cardiac-based filtering is the assumption that, on average and over several seconds of time, signal noise coming from real patient motion and other sources does not occur at the heart rate. As a result, the filters associated with this approach assume that noise is chaotic and random and in turn tend to find the underlying cardiac signal that is mixed with noise created by patient movement or other sources of artifact.

Another existing approach involves an oximeter having two light emitting diodes (LEDs), a red LED and an infrared LED, that alternatively illuminate an intravascular blood sample with two wavelengths of electromagnetic radiation. The electromagnetic radiation interacts with the blood and a residual optical signal is both reflected and transmitted by the blood. A photodiode in the light-to-frequency converter (LFC) collects oximetry data from the intravascular blood sample illuminated by the two LEDs. The LFC produces a periodic electrical signal in the form of a pulse train having a frequency, the logarithm of which is in linear relationship to the logarithm of the intensity of the optical signal received by the LFC. The data becomes an input to a high-speed digital counter, which converts the pulsatile signal into a form suitable to be entered into a central processing unit (CPU) of a computer system. Once inside the CPU, the time-domain data is converted into the frequency domain by, for example, performing the well-known Fast Fourier Transform (FFT) on the time-domain data. The frequency domain data is then processed to determine the saturation value.

In this approach, the magnitudes of the AC and DC components for both the red LED and the IR LED are determined using a frequency domain analysis. For both the red and infrared signals, the AC component is determined by the magnitude of the highest spectral peak found between 0.5 to 2.5 Hz. This highest peak represents the pulsatile, or AC component, of the oximetry waveform. Likewise, the magnitude of the DC component is the highest spectral peak generally found in the first bin at 0 Hz.

Another approach involves a system for processing signals containing information about the pulse rate and oxygen saturation of arterial blood flowing in tissue. To determine the pulse rate and oxygen saturation from the signals, the positive peaks, negative peaks, and period of the signal are determined. The disclosed invention accomplishes this by first searching for a sustained positive sloping region of the signal. Then the first derivative of the signal with respect to time is analyzed and points on the signal before and after the occurrence of a slope reversal are marked. If the slope at the first point is positive, the interval between the two points is searched for a maximum amplitude that is identified as a positive peak. After the occurrence of a negative sloping region of the signal, another pair of points are marked occurring before and after a subsequent slope reversal. The minimum amplitude of the signal between these points is then identified as a negative peak. These positive and negative peaks are then compared with waveform templates to determine whether the amplitude between the peaks falls within an allowable range and to determine whether the interval between the peaks likewise falls within an acceptable range. These ranges are adjustable in proportion to the amplitude and interval compared against them. In this manner, values for the positive peak, negative peak, and period of the signal can be determined.

Preferably, the output produced by the above-described derivative processor is the auto-normalized convolution derivative. This auto-normalization provides sufficient processing to discriminate peaks from inflections in the PPG, provided that the signal is a well-behaved function. In practice, physiological signals such as the PPG are not well behaved and are often modulated with artifacts due to noise, interference, and patient motion.

Another approach involves an ECG-synchronized pulse oximeter. The patent discloses a pulse oximeter, including a sensor for the emission and detection of two beams of light of different wavelengths. The beams are passed through skin tissue and modulated by the flow of blood therein. The preferred embodiment includes an apparatus for the amplification and detection of an ECG, R-wave signal. This signal is used as a reference to guide the averaging of subsequent optical pulse waveforms. The weight given to the newest pulse waveform during the averaging process is determined by the amplitude of that pulse waveform and by the degree of similarity between it and the preceding pulse waveform. The composite, averaged pulse waveform is then used in computing the oxygen saturation of the blood.

In light of the above-described disadvantages, there is need for methods and systems that remove asynchronous motion signals from synchronous cardiac signals superimposed in the photo-plethysmogram. Additionally, there is a need for a system that processes photo-plethysmographic signals in both time and frequency domains. Furthermore, there is a need for a system to generate a unique 'cardiac' morphology, which helps in separating cardiac signals from motion signals.

SUMMARY OF THE INVENTION

The present invention is directed toward an oximetry system employing a novel signal processing method. In one embodiment, a pulse oximetry system for the determination of a physiological parameter capable of removing motion artifacts from physiological signals comprises a hardware subsystem and a software subsystem.

The hardware subsystem comprises an optical sensor unit for providing the pulse oximetry system with a plurality of photo-plethysmographic data, wherein the sensor may either be transmittance or reflectance type containing at least two light emitting diodes for emitting light of two different wavelengths. The hardware subsystem additionally comprises a photo-detector for detecting the light after being transmitted or reflected by a patient's tissue, wherein the detected light is representative of the patient's photo-plethysmographic data, a microcomputer comprising an input/output unit, a processor for processing the photo-plethysmographic data, wherein the processor includes a control unit, a register unit, and an arithmetic and logic unit, and a memory unit, wherein the memory unit is operably coupled to the processor.

The software subsystem is used in conjunction with the hardware subsystem to perform a method for removing a plurality of motion artifacts from the photo-plethysmographic data and for obtaining a measure of at least one physiological parameter from said data. The method comprises acquiring the raw photo-plethysmographic data, transforming the data into the frequency domain, analyzing the transformed data to locate a series of candidate cardiac spectral peaks (primary plus harmonics), reconstructing a photo-plethysmographic signal in the time domain with only the candidate cardiac spectral peaks (primary plus harmonics), computing the second order derivative of the reconstructed photo-plethysmographic signal, analyzing the candidate second order derivative photo-plethysmographic signal to determine the absence or presence of cardiac physiologic signal characteristics, and finally selecting the best physiologic candidate from the series of potential cardiac spectral peaks (primary plus harmonics) based upon a second derivative scoring system. This scoring system is preferentially based upon second derivative processing analysis, but can be equally applied using the first, third, fourth or other similar derivative processing analysis.

In one embodiment, analyzing transformed data to locate candidate spectral peaks comprises the steps of assigning a largest power amplitude from said data as a primary candidate spectral peak and assigning a next largest power amplitude that is not a harmonic of said primary candidate spectral peak as a secondary candidate spectral peak. Further, the candidate spectral peaks detected during the analysis of transformed data is classified into Primary=$P_j$ and their respective Harmonics=$H_j$, where j=1, ..., m and wherein a maximum of m Primary frequencies are identified as candidate spectral peaks.

In one embodiment, the photo-plethysmographic signal is reconstructed by transforming data from a frequency domain data into a time domain by including only a plurality of primary candidate spectral peaks and a plurality of corresponding harmonic spectral peaks.

In one embodiment, the second order derivative photo-plethysmographic signal is analyzed to determine a plurality of parameters by performing a morphological analysis of the second order derivative photo-plethysmographic signal to determine a unique cardiac morphology, wherein the cardiac morphology consists of four systolic and one diastolic waves, and wherein the analysis accounts for a plurality of wave transitions. The second order derivative photo-plethysmographic signal analysis further comprises the step of performing a morphological analysis of the second order derivative photo-plethysmographic signal to determine at least one height of the wave transitions.

Optionally, the criterion for detecting a predefined type of wave transition among a first wave, a second wave, a third wave, a fourth wave, and a fifth wave comprises identifying the largest transition between a first wave and a second wave and determining whether a set of first, second, third, fourth, and fifth waves adhere to a formula: height (first wave to second wave)>{height (second wave to third wave), height (third wave to fourth wave), height (fourth wave to fifth wave)}.

Optionally, the removal of motion artifacts from the photo-plethysmographic signal comprises classifying a first primary-harmonic set with a first highest $score_j$ as a likely cardiac geometry and classifying a second primary-harmonic set with a highest $score_k$ as a likely motion geometry based upon wavelet analysis. This scoring system is preferentially based upon calculating correlation coefficients by applying Symlets #7, Daubechies #9 or Morlet wavelets to the second derivative of the candidate cardiac spectral peaks (primary plus harmonics), but can be equally applied using any other wavelet correlation coefficient scoring system. The candidate cardiac spectral peaks (primary plus harmonics) that have the highest wavelet correlation coefficient thus becomes the chosen physiologic cardiac spectral peaks.

These and other aspects of the invention shall be described in further detail with reference to drawings and in the Detailed Description.

BRIEF DESCRIPTION OF THE DRAWINGS

These and other features and advantages of the present invention will be appreciated, as they become better understood by reference to the following Detailed Description when considered in connection with the accompanying drawings, wherein.

DETAILED DESCRIPTION

The present invention discloses methods and systems for removing asynchronous motion artifacts from synchronous cardiac signals by performing second order derivative processing of the measured photo-plethysmographic waveforms. The present invention will be described with reference to the aforementioned drawings. One of ordinary skill in the art would appreciate that the application described herein is an example of how the broader concept can be applied.

Figure 1A:
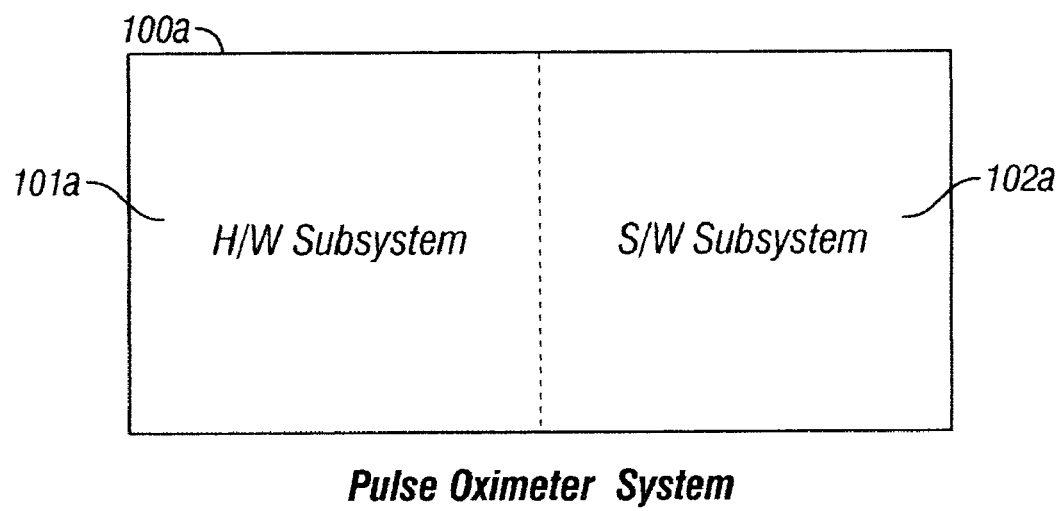
FIG. 1a is a schematic of an exemplary pulse oximetry system.

Referring to FIG. 1a, a system embodiment of the pulse oximeter 100a of the present invention is shown. The pulse oximeter system 100a comprises of a hardware subsystem 101a and an associated software subsystem 102a. The hardware subsystem 101a performs signal acquisition, followed by measurements and optional preconditioning. The software subsystem 102a is responsible for discarding motion artifacts from the acquired, measured and optionally preconditioned signal. Within the software subsystem 102a resides a method embodiment (not shown). of this invention, which includes a series of steps that exploit certain characteristics of photo-plethysmographic waveforms.

Figure 1B:
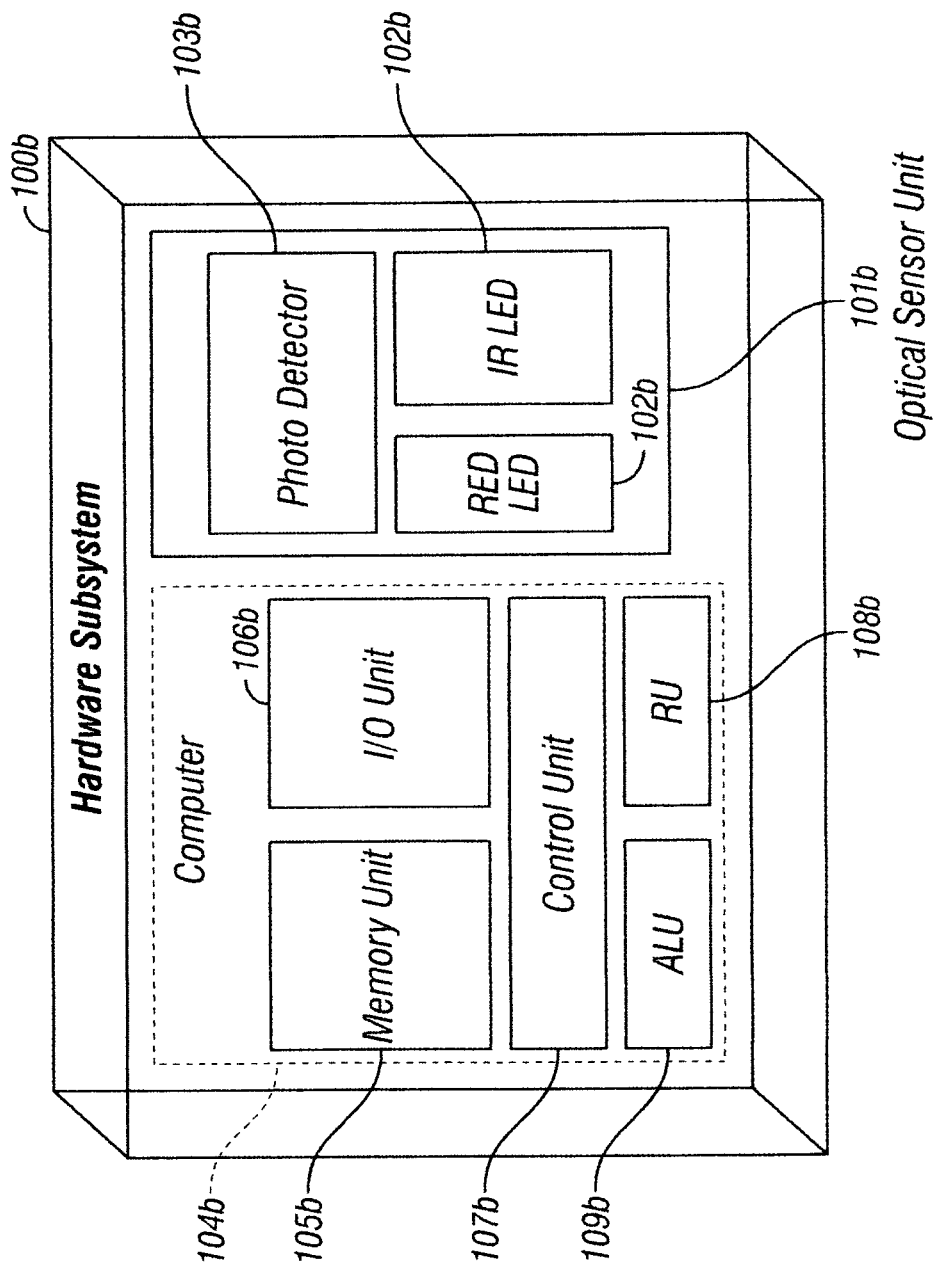
FIG. 1b depicts one embodiment of a hardware subsystem of an exemplary pulse oximetry system.

FIG. 1b shows a detailed view of the hardware subsystem. The hardware subsystem 100b incorporates an optical sensor unit 101b containing red and infrared light emitting diodes or RED and IR LEDs 102b, a photo-detector 103b, and a microcomputer 104b. The sensor 101b is positioned in contact with the finger of a patient and provides the aforesaid pulse oximeter system with red and infrared photo-plethysmographic waveforms. The sensor 101b may either be transmittance or reflectance type.

The microcomputer 104b comprises of a memory unit 105b, an I/O unit 106b, a control unit 107b, a register unit 108b and an arithmetic and logic unit 109b. It may be noted here that the memory unit 105b accommodates the aforesaid software subsystem.

Figure 1C:
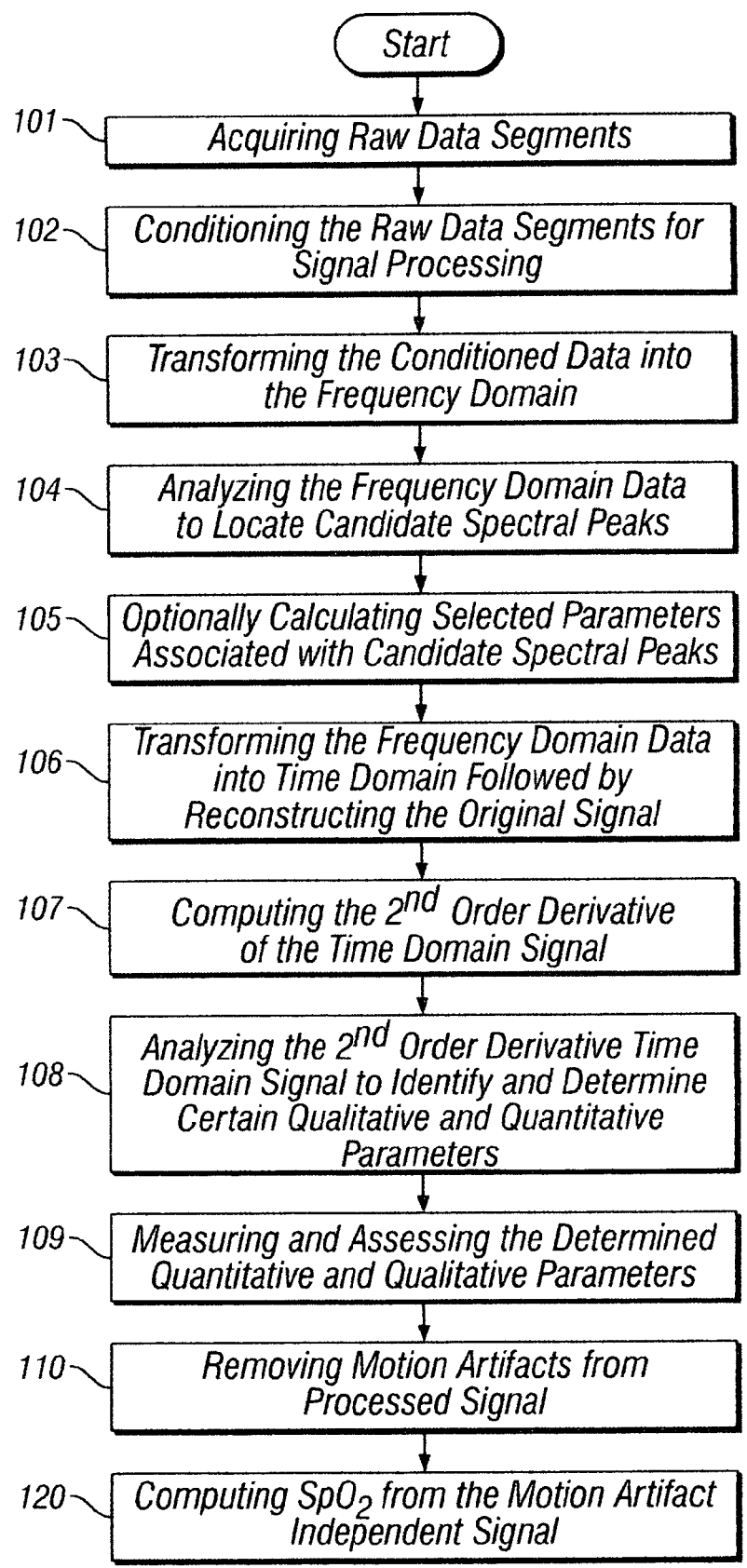
FIG. 1c is an embodiment of a process employed by the present invention.

FIG. 1c is a flowchart depicting a process employed in the present invention for removing motion artifacts from photo-plethysmographic data and obtaining a measure of pulse rate and $SpO_2$ from that data. The algorithm includes the steps of acquiring segments of the raw photo-plethysmographic data 101, both a RED data segment and an IR data segment from the aforesaid sensor, conditioning each segment of acquired raw photo-plethysmographic data for signal processing 102, transforming the conditioned data into the frequency domain 103, analyzing the frequency domain data to locate candidate spectral peaks 104, optionally calculating selected parameters associated with the candidate spectral peaks 105, transforming the frequency domain data into time domain followed by reconstructing the original photo-plethysmographic data or signal 106, computing the $2^{nd}$ order derivative of the time domain photo-plethysmographic signal 107, analyzing the $2^{nd}$ order derivative time domain photo-plethysmographic signal for the identification and determination of its certain qualitative and quantitative parameters 108, measurement and assessment of the quantitative and qualitative parameters determined and/or identified previously 109, removal of motion artifacts from processed photo-plethysmographic signal 110, and eventually computing $SpO_2$ for the motion artifact independent photo-plethysmographic signal 120. The operations 106, 107, 108, and 109 are repeated for each (1 . .

m) Primary-Harmonic sets of the candidate spectral peaks located earlier. This method is applied to both RED and IR data signals to eliminate or reduce noise and/or artifacts from the data signals prior to outputting pulse rate and SpO₂.

Referring to FIGS. 1b and 1c, the method of this invention begins with an initial step of acquiring a segment of raw photo-plethysmographic data (e.g., approximately 37 seconds duration) measured from any one of the two LEDs 102b. During this step light (RED or IR) from the LED 102b is transmitted through a finger and is further detected with a photo-detector 103b on the opposite side of the finger. This step of acquiring a raw photo-plethysmographic data segment is depicted by block 101 FIG. 1c.

Figure 2:
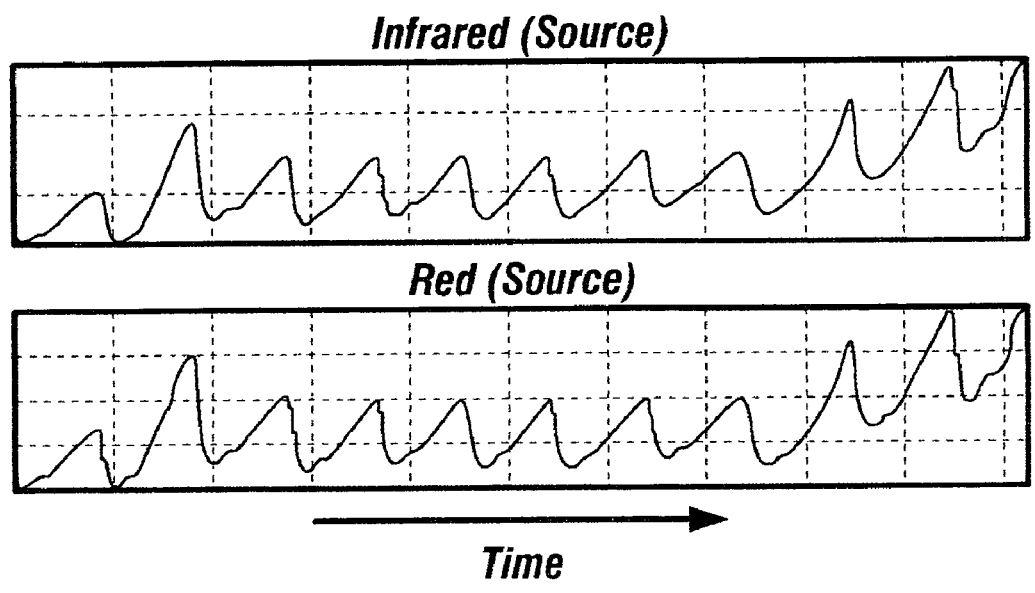
FIG. 2 illustrates sample segments of acquired IR and RED photo-plethysmographic data.

FIG. 2 illustrates sample segments of IR and RED photo-plethysmographic data acquired according to block 101. The horizontal axis of FIG. 2 is measured in units of time, and illustrated here in seconds. The vertical axis of FIG. 2 is measured in arbitrary units, and illustrated here in analog-to-digital output units. For convenience, a 37 seconds segment of data will be used to illustrate the method. It should be readily apparent to one of ordinary skill in the art that the method of the invention is not limited to data segments of this size. The signal processing steps described herein may be performed on both RED and IR photo-plethysmographic data segments independently and simultaneously. Thus, while the steps of the method may be illustrated with data from an IR radiation signal, the same steps are applicable to data from a RED light signal and vice versa.

A segment of data may be received from a sensor that converts transmitted or reflected light signals into electrical signals. A photo-detector, for example, a photodiode, may be used to receive a RED and IR photo-plethysmographic data from the sensor. The collected signals may then be pre-conditioned, for example by filtering or amplifying, and converted into digital data using an analog-to-digital converter for subsequent digital signal processing. The RED and IR photo-plethysmographic data or waveforms may be sampled at any convenient data rate. However, for simplicity of illustration, a sampling rate of 27.5 Hz will be performed on the 37 seconds segment of RED and IR photo-plethysmographic data. A 37 seconds segment of data corresponds to approximately 1024 data points with a sampling rate of 27.5 data points per second.

Figure 3:
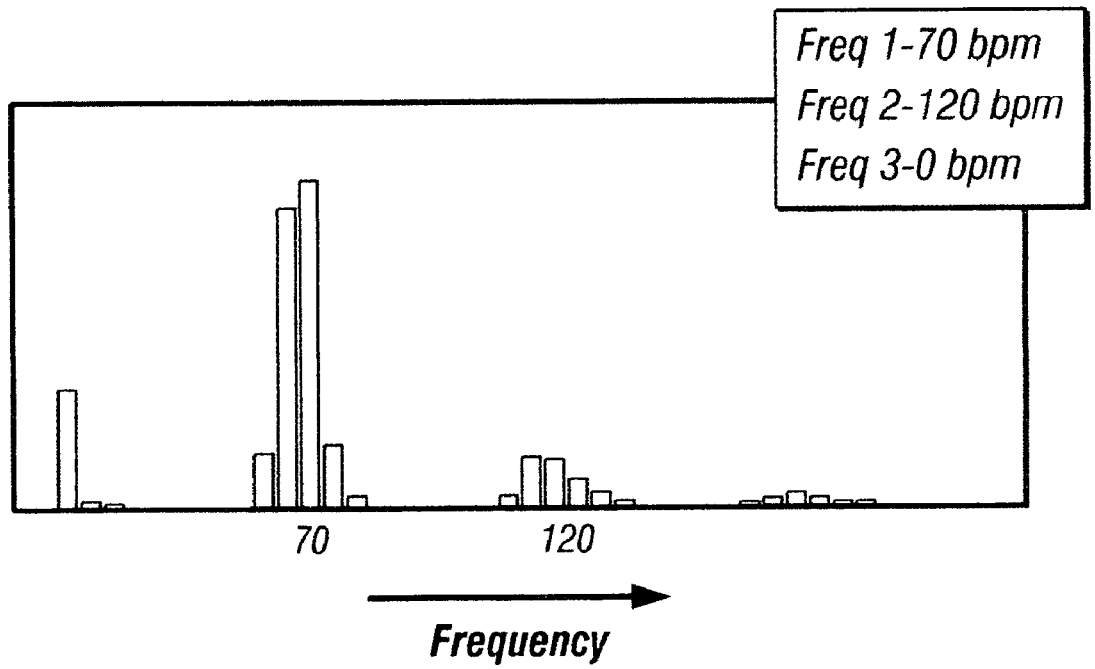
FIG. 3 illustrates a power spectrum of an IR photo-plethysmographic data segment.

Once a segment of data from a single electrical signal due to IR radiation signal or RED light has been acquired and digitized, it may be conditioned for subsequent signal processing, as depicted by block 102 of FIG. 1c. Signal conditioning may include filtering to reduce spectral leakage resulting from subsequent frequency analysis. There are several window filters that may be suitable for such purposes. For example, and not by way of limitation, a Hanning window may be used to reduce spectral leakage. It will be readily apparent to one of ordinary skill in the art of digital signal processing that other window filters and methods of filtering data to reduce spectral leakage may be selected. As such methods of filtering and various filters are known to one of ordinary skill in the art of signal processing, they will not be further detailed herein. FIG. 3 illustrates the power spectrum of the IR photo-plethysmographic data segment of FIG. 2 after filtering and transforming. The vertical axis of FIG. 3 may be measured in any arbitrary units of power. The horizontal axis is measured in any units of frequency, specifically here in the units of bpm (beats per minute).

The conditioned data is then transformed into the frequency domain for further analysis and signal processing. Signal processing as described herein is generally performed in the frequency domain. The segment of data is converted into the frequency domain by, for example, performing Fast Fourier Transform (FFT) on the data segment. FIG. 3 is a graph of the FFT of the IR data segment of FIG. 2. FIG. 3 illustrates a primary candidate spectral peak at a frequency of approximately 70 bpm and a secondary candidate spectral peak at a frequency of approximately 128 bpm. Other common techniques of converting. time-domain data to the frequency domain may also be used, e.g., classical methods using the FFT such as the periodogram or correlogram, autoregressive methods, Prony's method, minimum variance methods, maximum likelihood methods. Additionally, time domain data may be converted to the frequency domain using transforms such as discrete cosine transform, wavelet transform, discrete Hartley transform, and Gabor transform. The preferred transform according to this method is the FFT with a window size of 1024 points. The 1024 data points are placed in a buffer, the FFT buffer. The FFT transforms the 1024 points of data from the time domain into the frequency domain.

The output of the FFT is 512 points of real and 512 points of imaginary data in the frequency domain. From these 512 points of real and 512 points of imaginary data the power spectrum is calculated and placed in a power spectrum buffer.

Both transient and periodic artifacts can induce peaks in the frequency domain. Analyzing the power spectrum to locate candidate spectral peaks is depicted in block 104 of FIG. 1c. Numerous approaches towards determination of peaks in the frequency domain are already known in the prior art. For example, one such approach utilizes first derivative processing for the determination of positive slope and positive/negative peak in a photo-plethysmogram. Another approach towards determination of candidate spectral peaks in a photo-plethysmogram would be to order the frequencies by peak amplitude from largest to smallest, F1 to $F_m$, where F1 through $F_m$ are not Harmonics of each other, and analyze them one by one. However, the preferred approach selects up to three candidate spectral peaks for further analysis.

Candidate spectral peaks are located from the power spectrum computed in block 103. The power spectrum buffer is an array of 512 vector points (referred to herein as "bins") in the frequency domain. Each array element in the power spectrum buffer represents the power of the corresponding frequency in the original raw photo-plethysmographic waveform. Of the 512 bins, only bins 5 (29 bpm) through 43 (252 bpm) are of interest, since this range covers the physiological limits of the human heart rate. This set of 43−5+1=39 bins forms the set of bins selected for subsequent analysis. All other bins are unused by the method of the invention because they cannot physiologically represent a valid spectral frequency of a pulse rate. Table 1, below, shows the first 45 points of the power spectrum buffer or array.

TABLE 1

| Power Spectrum Buffer bin number n | Frequency (Hz) f = n * 100/1024 | Pulse Rate (bpm) Pulse Rate = f * 60 |
|---|---|---|
| 0 | 0.00000 | 0.0 |
| 1 | 0.09766 | 5.9 |
| 2 | 0.19531 | 11.7 |
| 3 | 0.29297 | 17.6 |
| 4 | 0.39063 | 23.4 |
| 5 | 0.48828 | 29.3 |
| 6 | 0.58594 | 35.2 |
| 7 | 0.68359 | 41.0 |
| 8 | 0.78125 | 46.9 |
| 9 | 0.87891 | 52.7 |
| 10 | 0.97656 | 58.6 |
| 11 | 1.07422 | 64.5 |

TABLE 1-continued

| Power Spectrum Buffer bin number n | Frequency (Hz) f = n * 100/1024 | Pulse Rate (bpm) Pulse Rate = f * 60 |
|---|---|---|
| 12 | 1.17188 | 70.3 |
| 13 | 1.26953 | 76.2 |
| 14 | 1.36719 | 82.0 |
| 15 | 1.46484 | 87.9 |
| 16 | 1.50250 | 93.8 |
| 17 | 1.66016 | 99.6 |
| 18 | 1.75781 | 105.5 |
| 19 | 1.85547 | 111.3 |
| 20 | 1.95313 | 117.2 |
| 21 | 2.05078 | 123.0 |
| 22 | 2.14844 | 128.9 |
| 23 | 2.24609 | 134.8 |
| 24 | 2.34375 | 140.6 |
| 25 | 2.44141 | 146.5 |
| 26 | 2.53906 | 152.3 |
| 27 | 2.63672 | 158.2 |
| 28 | 2.73438 | 164.1 |
| 29 | 2.83203 | 169.9 |
| 30 | 2.92969 | 175.8 |
| 31 | 3.02734 | 181.6 |
| 32 | 3.12500 | 187.5 |
| 33 | 3.22266 | 193.4 |
| 34 | 3.32031 | 199.2 |
| 35 | 3.41797 | 205.1 |
| 36 | 3.51563 | 210.9 |
| 37 | 3.61328 | 216.8 |
| 38 | 3.71094 | 222.7 |
| 39 | 3.80859 | 228.5 |
| 40 | 3.90625 | 234.4 |
| 41 | 4.00391 | 240.2 |
| 42 | 4.10156 | 246.1 |
| 43 | 4.19922 | 252.0 |
| 44 | 4.29688 | 257.8 |

In table 1, column 1 is the bin number, n; column 2 is the center frequency, f of the corresponding bin number, n, calculated here as the product of the bin number n and sampling rate (100 samples/sec) divided by the block size used by the FFT (i.e., 1024); and column 3 is the pulse rate corresponding to the center frequency, f, calculated by multiplying f (measured in units of beats per second) by 60 to convert to units of beats per minute (bpm). Although the sampling rate selected here is 100 samples/sec, it is not limited to this value. The center frequency values corresponding to a sampling rate of 27.5 Hz can be similarly calculated as the product of the bin number n and the sampling rate 27.5 Hz divided by the block size of the FFT used, i.e. 1024.

In order to select candidate spectral peaks (and corresponding frequencies), different amplitude analysis methods are applied to different frequency bands. The amplitude of adjacent and nearby frequency components of the candidate spectral peak amplitude may be compared in terms of their absolute or relative values. For example, the frequencies represented by candidate bins 5 through 10 ("5-10" search method) may be stepped through in a sequential fashion.

In one embodiment, a "5-10" search method is employed. According to this method, a candidate bin is assumed to be a candidate power spectrum peak if the previous three bins and subsequent four bins relative to a candidate bin are all lower in power than the candidate bin. For example, in order for bin 6 to be a candidate spectral peak, bins 3, 4, 5, 7, 8, 9 and 10 must all be lower in power than bin 6. The terms "spectral peak", "power peak", "power spectrum peak" or "peak" are used synonymously herein. Various amplitude, shape, and syntactic or other pattern analysis methods may be applied to identify a candidate peak. Also, multiple curve fit methods, as known to one of ordinary skill in the spectroscopic analysis, may also be applied.

In a second embodiment, a first derivative criteria to select candidate spectral peaks within a given power spectrum is used. Using an assumption that a candidate spectral peak is defined as the frequency bin at which the slope is zero, therefore employing the first derivative criterion for the detection of extreme or critical points (i.e. points at which slope is zero), all such frequency bins are firstly detected. It is known to one of ordinary skill in the art that the criterion for verification of "maxima and minima" can be given by the following equations (A) and (B):

$$(d^2y/dx^2) \text{ or } (d^2f(x)/dx^2) > 0 \rightarrow \text{for minima if slope } (dy/dx) = 0 \text{ at the detected extreme or critical point;} \text{ and} \quad (A)$$

$$(d^2y/dx^2) \text{ or } (d^2f(x)/dx^2) < 0 \rightarrow \text{for maxima if slope } (dy/dx) = 0 \text{ at the detected extreme or critical point.} \quad (B)$$

This eventually leads to the determination of all candidate. spectral peaks. Once the power spectrum peak candidates or candidate spectral peaks are found, predetermined criteria are applied to select a plurality, preferably three, candidate spectral peaks.

Referring back again to the embodiment utilizing the "5-10" search method, a power peak associated with a largest power amplitude is selected to be the primary candidate spectral peak. Then, any power peaks that are determined to be harmonics of the primary candidate spectral peak are collected to form a first Primary-Harmonics set. In general, a Primary-Harmonic set is symbolically represented as $\{P_j, H_j\}$, where $P_j$ is the Primary frequency corresponding to a primary candidate peak whereas $H_j$ is its respective Harmonic. According to this method, a Harmonic is defined as any power peak the frequency of which is a multiple of the primary candidate peak and the amplitude of which is less than half the maximum allowed power of the previous Harmonic, or in the case of the first Harmonic, less than half the power of the primary peak. For example, assume a primary candidate peak is found at bin 10.

Possible harmonic bins of 10 are bins 19-21, 29-31 and 39-41. Continuing with the example, if the primary power peak amplitude (bin 10) is 100 arbitrary power spectrum units, then bins 19-21 must be less than 50 units to be deemed a harmonic, bins 29-31 must be less than 25 units and bins 39-41 must be less than about 12 units, where units are the measure of the amplitude of the power spectrum. Other weights may be applied to the analysis of the sequence for detection of Harmonics of the candidate spectral peak without departing from the scope of the invention.

After Harmonics of the primary candidate spectral peak possessing the largest power amplitude are collected into a first Primary-Harmonic set, the next largest remaining power peak found (if any) is selected to be the secondary candidate spectral peak. Again, the Harmonics corresponding to the secondary candidate spectral peak are collected to form a second Primary-Harmonics set.

Finally, if the previous pulse rate is non-zero, the power spectrum corresponding to the previous pulse rate is determined. If the bin corresponding to the previous pulse rate is not equal to the primary or secondary candidate power peak, then the bin corresponding to the previous pulse rate is selected to be the tertiary candidate spectral peak. Next, the Harmonics corresponding to the tertiary candidate spectral peak are collected into a third Primary-Harmonic set. Thus, three candidate spectral peaks (primary, secondary and tertiary) and corresponding frequencies of each candidate peak are identified. It may be noted that any number of candidate spectral peaks may exist and therefore less than or more than three candidate spectral peaks can be selected for further analysis. Assuming that a maximum of m Primary frequencies are identified as candidate spectral peaks, then these peaks are classified into Primary $P_j$ and their respective Harmonics $H_j$ where $j=1, \ldots, m$.

Optionally, selected parameters associated with the candidate spectral peaks may be calculated and may include pulse window filtering, calculating such parameters as peak detection and pulse rejection criteria and determining descriptive parameters associated with each of the candidate spectral peaks. These parameters are used to determine a pulse confidence for each candidate spectral peak. The parameters calculated herein for each filtered candidate spectral peak include measures of central tendency and variability of pulse width, pulse rate and $SpO_2$, as well as measures of the history and confidence of these parameters. It should be noted that other parameters including, but not limited to, other measures of central tendency, variability (i.e., skewness, kurtosis), history/trend and confidence could be calculated from the candidate spectral peaks.

Prior to calculating the aforementioned parameters, each candidate spectral peak is filtered with a narrow band filter, such as a bandpass, finite impulse response (FIR) filter. In one aspect of the present invention, one of several predefined FIR filters is applied to a given bin or candidate peak. The peak frequencies of the filters may be separated by a fixed difference in frequency (measured in Hz or bpm), such as 25 bpm, or may be variable and a function of either frequency or a characteristic of the spectrum, for example variability or noise, or both. For example, if a candidate peak was found at bin 12, a filter with center or peak frequency of 76.2 bpm might be chosen. A fixed difference in frequency may be in a range from about 15 bpm to about 40 bpm. A variable difference in frequency may be in a range from about 15 bpm to about 40 bpm.

Preferably, to improve discrimination, especially with closely spaced peaks, the bandpass filter coefficients may be stored or generated and adjusted as needed so that the center frequency is nearly identical to the candidate frequency. Additionally, other filtering methods such as (a) other types of bandpass filters, i.e., infinite impulse response (IIR) filters, and (b) frequency domain methods such as transforming the data into the frequency domain (for example, FFT), filtering or eliminating unwanted components in the frequency domain and transforming back into the time domain (for example, inverse FFT) for further signal processing, may be applied.

Having identified a set of m Primary frequencies as candidate spectral peaks ($P_j$) and their respective Harmonics ($H_j$) where $j=1, \ldots, m$, the frequency domain data is converted into the time domain, i.e. previously identified Primaries $P_j$ and their respective Harmonics $H_j$ are transformed back into the time-domain.

One preferred approach employs the Inverse Fast Fourier Transform or IFFT. The output of IFFT is the time-domain analogue of the Primary $P_j$ and their respective Harmonics $H_j$. Further, a set $(1 \ldots m)$ time-domain $PPG_j$ is reconstructed by including only the Primary $P_j$ and their respective Harmonics $H_j$. It is obvious to a person of ordinary skill in the art of signal processing that numerous methods or techniques concerning signal reconstruction in the time as well as frequency-domain are already known. One exemplary embodiment employs the sinc approximation method. This is not a limitation, however, and other possible methods for reconstructing a signal in the time-domain will also suffice. Because methods of transforming frequency-domain data to time-domain are known to one of ordinary skill in the art of signal processing, they will not be further detailed herein.

Once a set of $(1 \ldots m)$ time-domain $PPG_j$ signals is reconstructed as explained above the $2^{nd}$ order derivative of each $(1 \ldots m)$ time-domain $PPG_j$ $(=d^2IFFT_j)$ is computed. A preferred embodiment utilizes the numerical differentiation approach for finding the $2^{nd}$ order derivative of each $(1 \ldots m)$ time-domain $PPG_j$ $(=d^2IFFT_j)$. The numerical differentiation of digitized signals (or signal comprising discrete samples) is a well-known approach towards finding signal derivatives. It will be readily apparent to one of ordinary skill in the art of signal processing that other possible approaches towards finding signal derivatives may be selected. Because approaches of finding signal derivatives are already known to one of ordinary skill in the art of signal processing, they will not be further detailed herein.

The $2^{nd}$ order derivative of PPG signals or a second order derivative photo-plethysmogram (SDPTG) is computed because, in the domain of the SDPTG, the cardiac signal exhibits a unique 'cardiac' morphology. The SDPTG or an acceleration photo-plethysmogram (APG), as it is sometimes called, is obtained by computing the $2^{nd}$ order derivative of a given photo-plethysmogram or PPG signals. The SDPTG facilitates efficient qualitative and quantitative morphological analysis of physiological signals since it visually represents physiological changes and other artifacts, better than that of normal waves.

Figure 4A:
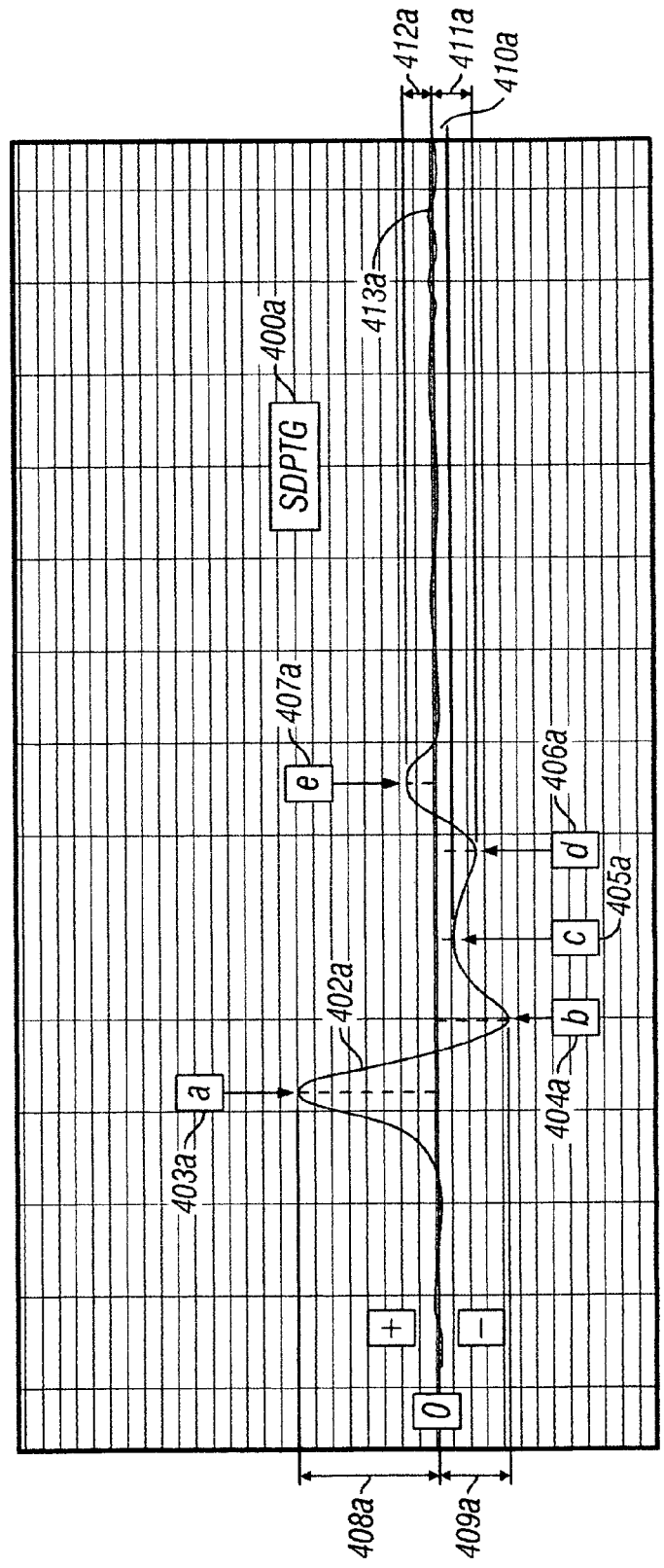
FIG. 4a is a graphical illustration of a second order derivative of a photo-plethysmogram.

Referring to FIG. 4a, a graphical illustration of a SDPTG or APG 400a is plotted. A qualitative morphological analysis of the SDPTG 400a reveals that, in the domain of SDPTG 400a, a cardiac signal 402a exhibits a unique cardiac morphology. This unique cardiac morphology consists of a first set of 4 systolic waves and a second set of 1 diastolic wave. More specifically, the first set of 4 systolic waves is constituted by two positive waveforms namely, a-wave 403a and c-wave 405a, and two negative waveforms namely, b-wave 404a and d-wave 406a respectively. On the other hand the second set of 1 diastolic wave is constituted by a diastolic waveform namely, e-wave 407a. Further, the a-wave 403a is an actual representation for an initial diastolic wave, b-wave 404a an actual representation for an early negative wave, c-wave 405a for a re-increasing wave, d-wave 406a for a re-decreasing wave and e-wave 407a for a diastolic wave respectively.

Another significant qualitative parameter that is taken into consideration is wave transition. A set of possible wave transitions can be taken into consideration for subsequent calculation of a quantitative parameter namely, height of a wave transition.

During a quantitative morphological analysis of the SDPTG 400a, a set of heights 408a, 409a, 410a, 411a and 412a of the waves 403a, 404a, 405a, 406a, and 407a are measured from the baseline 413a. Heights above the baseline 413a are considered positive while the heights below the baseline 413a are considered negative. A ratio b/a is calculated as the ratio of the height of the b-wave 404a is to the height of the a-wave 403a. Similarly, another ratio d/a is calculated as the ratio of the height of the d-wave 406a is to the height of the a-wave 403a. These ratios, b/a and d/a, are expressed in terms of percentage. In order to support further quantitative analysis of the SDPTG 400a, an aging index, is defined as per the following equation:

$$\text{Aging Index} = (b-c-d-e)/a.$$

Figure 4B:
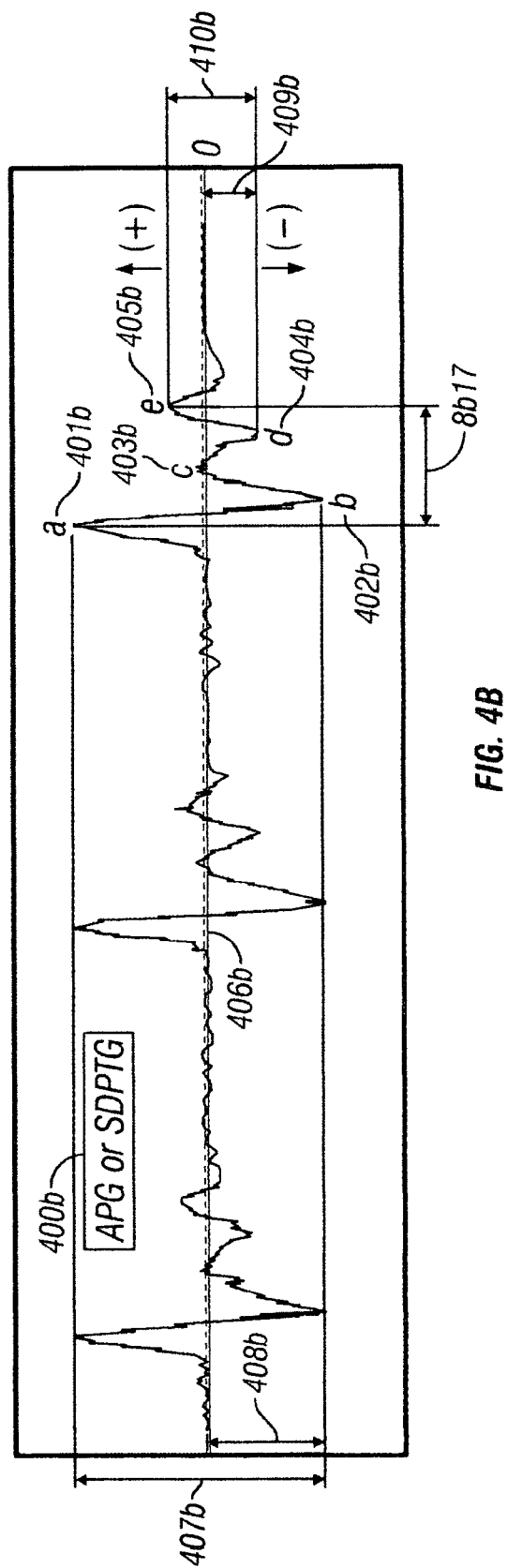
FIG. 4b is another graphical illustration of a second order derivative of a photo-plethysmogram.

Referring to FIG. 4b, the wave transitions that are taken into consideration are following: a first wave transition namely, (a-wave 401b)→(b-wave 402b), a second wave transition namely, (b-wave 402b)→(c-wave 403b), a third wave transition namely, (c-wave 403b→d-wave 404b), and a fourth wave transition namely, (d-wave 404b→e-wave 405b)

respectively. The heights of these wave transitions are measured from baseline 406b. The height of transition (a-wave 401b)→(b-wave 402b) is 407b, of (b-wave 402b)→(c-wave 403b) is 408b, of (c-wave 403b→d-wave 404b) is 409b and that of (d-wave 404b→e-wave 405b) is 410b.

After the calculation of heights of transitions such as (a-wave 401b)→(b-wave 402b), (b-wave 402b)→(c-wave 403b), (c-wave 403b→d-wave 404b) and (d-wave 8b04 →e-wave 8b05), they are compared amongst each other for the largest wave transition utilizing a predetermined criterion. In here, the criterion for finding the largest wave transition is as follows: Height [(a-wave 401b)→(b-wave 402b)] >{Height [(b-wave 402b)→(c-wave 403b)], Height [(c-wave 404b)→(d-wave 405b)], Height [(d-wave 405b)→(e-wave 406b)]}. In this case, the largest wave transition when estimated in terms of height of wave transition is 407b of the wave transition (a-wave 401b)→(b-wave 402b), as seen in FIG. 4b. It may be noted that the above-mentioned criterion for finding the largest wave transition is in no way a limitation and other suitable predetermined criterion may also be employed. This task of finding the largest wave transition is repeated for in each (1 . . . m) array $d^2$ $IFFT_j$ by utilizing the same predetermined criterion, as mentioned earlier.

It may be noted here that the unique cardiac morphology will be referred hereinafter as a-b-c-d-e segment. If an individual a-b-c-d-e segment meets the above-mentioned predetermined criteria, it is identified as a cardiac pulse morphology/geometry. The number of such cardiac pulse geometries counted over a 37 second window of $d^2IFFT_j$ are stored in an array $Score_j$. For example, $Score_1$ keeps record of the aggregate number of such cardiac pulse morphologies/geometries within an array $d^2IFFT_1$, i.e. the first array of (1 . . . m) $d^2IFFT_1$. Similarly, $Score_2$ keeps record of the aggregate number of such Cardiac pulse morphologies/geometries within an array $d^2IFFT_2$ and so on.

Referring back to FIG. 1c, after the completion of step 109, the operations associated with steps 106, 107, 108, and 109 are repeated for each (1 . . . m) Primary-Harmonic sets of the candidate spectral peaks located in step 104 to yield respective $Score_j$. After this each cardiac pulse geometry $Score_j$ is analyzed for the highest number of such Cardiac pulse geometries. In step 110, the $\{P_j, H_j\}$ set with the highest $Score_j$ is classified as the most likely cardiac geometry. Whereas another $\{P_k, H_k\}$ set with the highest $Score_k$ is classified as the most likely motion geometry.

In step 120, the elements of the $\{P_k, H_k\}$ set with the highest $Score_j$ classified as the most likely cardiac geometry are used for $SpO_2$ computation via AC/DC ratios from similar data collected at different wavelengths of light. It may be noted in context of the present invention two different wavelengths namely, RED and IR, were selected initially. The $SpO_2$ algorithm is described and is outlined here in FIG. 5.

Figure 5:
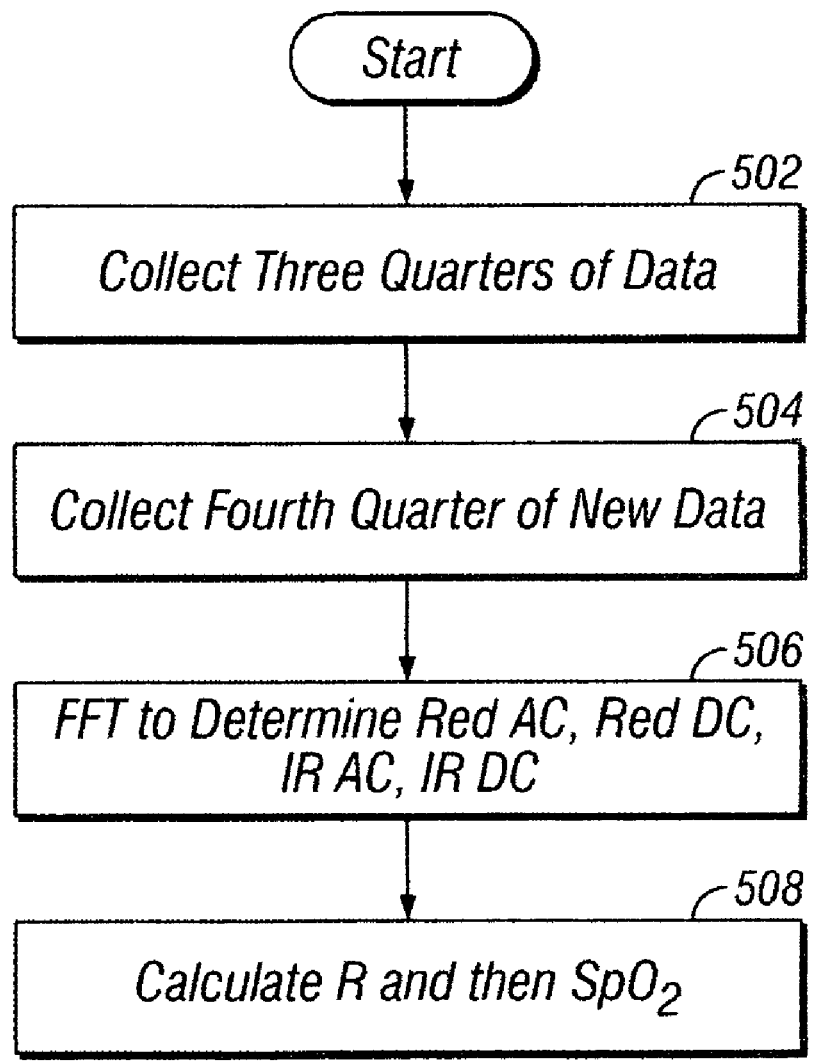
FIG. 5 is process for calculating $SpO_2$.
Figure 6A:
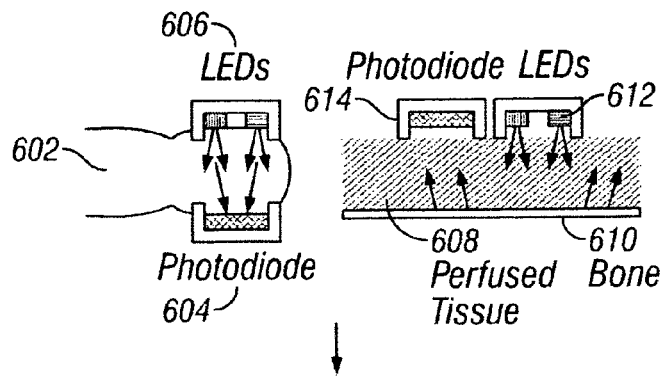
FIGS. 6a-6d depict another embodiment of a process employed by the present invention.
Figure 6A:
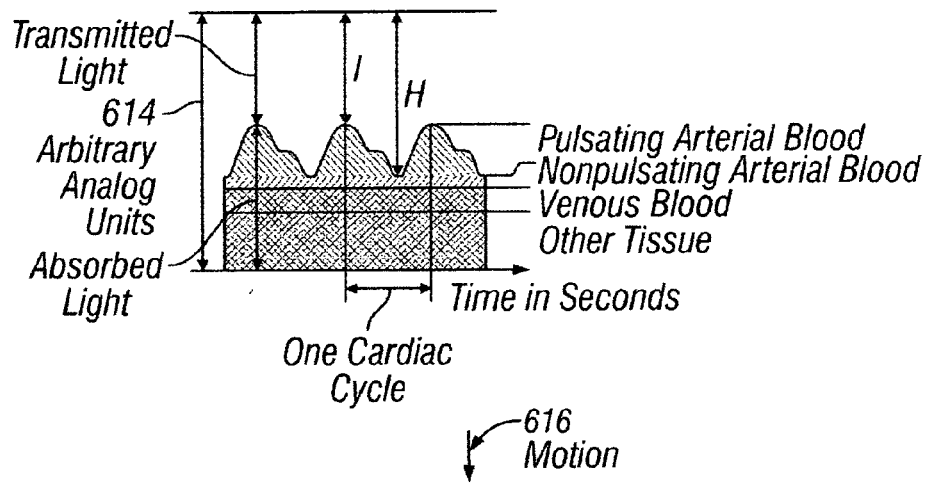
Figure 6A:
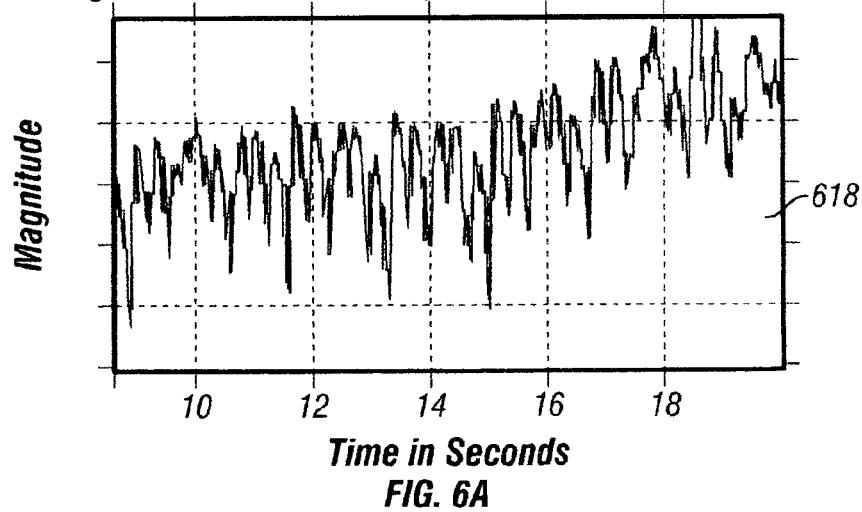
Figure 6B:
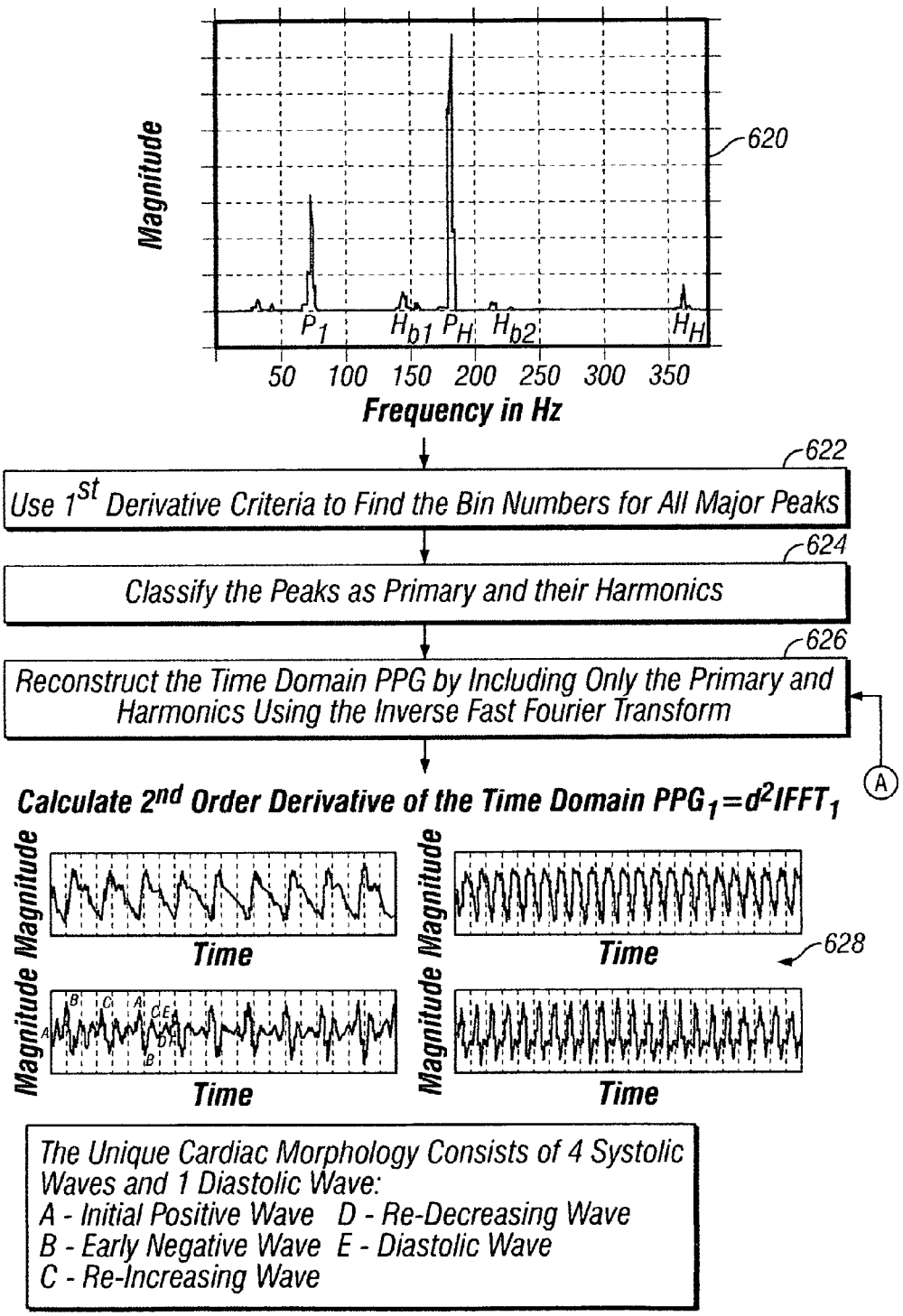
Figure 6C:
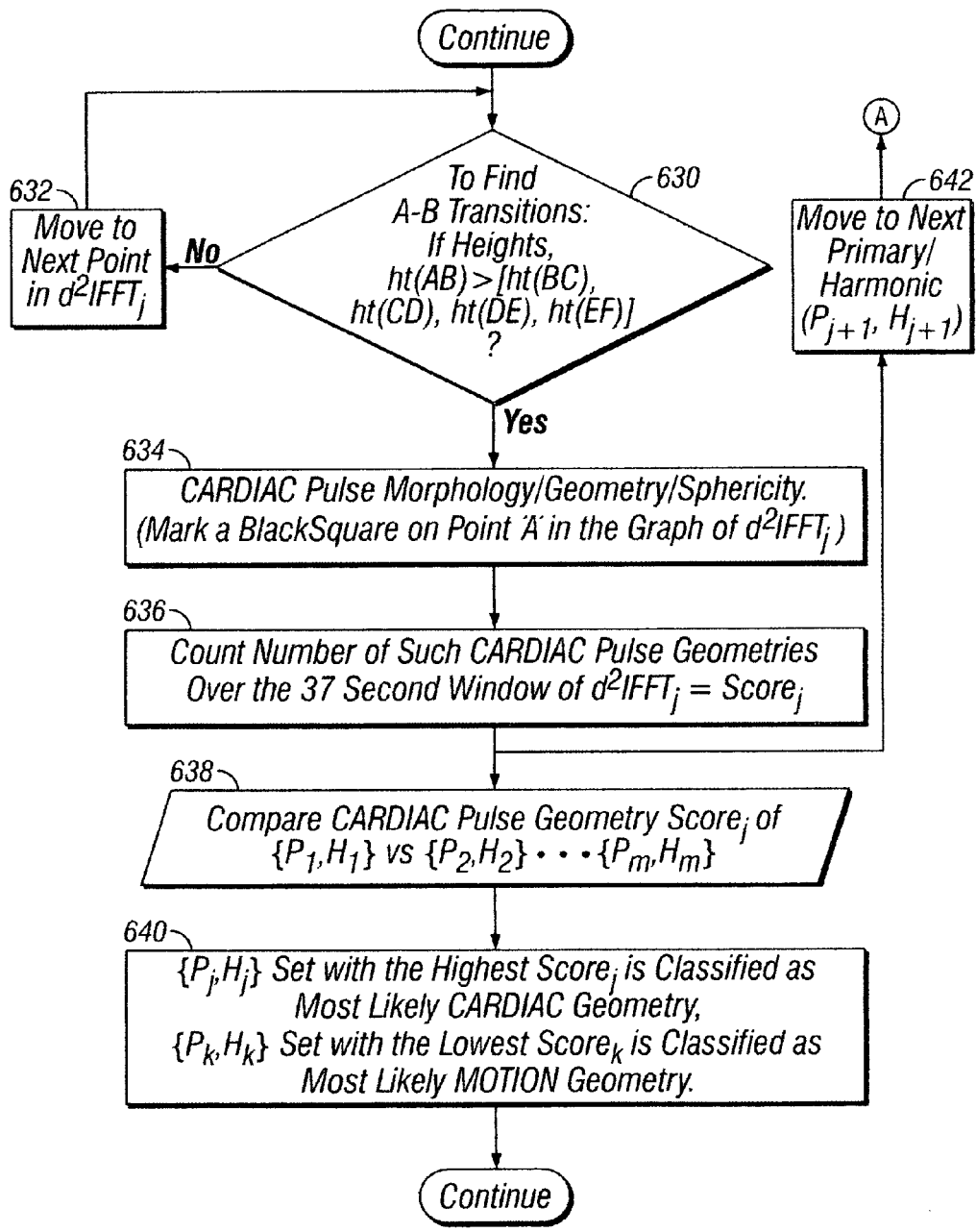
Figure 6D:
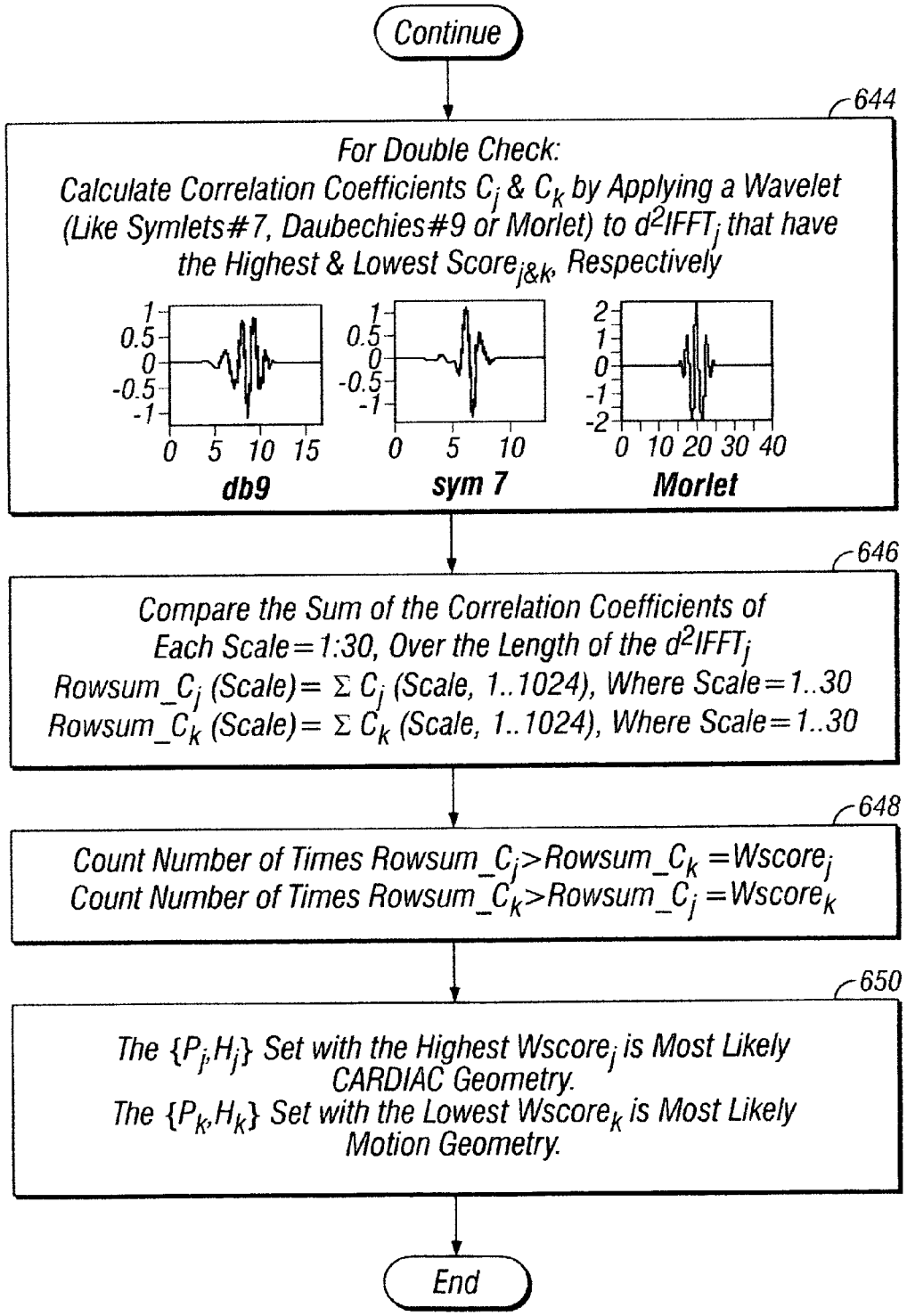

Referring to FIG. 5, data collection begins at 502. The total collection period is 37 seconds in this embodiment, which is divided into four quarters of approximately 9.25 seconds each. As shown at 502, three quarters (approximately 27.75 seconds) of data samples are collected to help initialize a sliding window function, described below. Next, the fourth quarter of the total sample (approximately 9.25 seconds worth of samples) is taken, at 504. The sample rate and time of collection are all variable. In this embodiment, between the samples taken at 502 and 504, a total of 37 seconds worth of samples are collected for processing. The samples can be taken at many rates, e.g., 15 Hz to 240 Hz, depending on the processing to take place below, as is known in the art. In the current embodiment the sampling rate is 27.5 Hz.

The $SpO_2$ algorithm then determines the magnitudes of the AC and DC components for both the RED LED 102b and the IR LED 102b of FIG. 1b ($AC_{red}$, $DC_{red}$, $AC_{ir}$, and $DC_{ir}$) using a frequency domain analysis 506. Specifically, the 37 seconds of time-domain data is converted into the frequency domain by performing a Fast Fourier Transform (FFT). The FFT can be performed in many ways. For example, an FFT of between 64 points (on data sampled at 15 Hz) and 1024 points (on data sampled at 240 Hz) will suffice. For both the RED and IR signals, the AC component is determined by the magnitude of the highest spectral peak found at from 0.5 to 2.5 Hz and represents the pulsatile, or AC component, of the oximetry waveform. Likewise, the magnitude of the DC component is the highest spectral peak found at from between 0.0 and 0.5 Hz.

An R-value may then be calculated from the RED and IR AC and DC spectral peaks, based on the formula:

$$R=(AC_{red}/DC_{red})/(AC_{ir}/DC_{ir})$$

Finally, $SpO_2$ value may be obtained from the approximate formula:

$$SpO_2=-25R+110.$$

In another embodiment of the present invention, as shown in FIGS. 6a through 6d, a transmission or reflectance type pulse oximeter acquires raw photo-plethysmogram data. Exemplary pulse oximeters comprise LEDs 606, 612 emitting light, which enters through tissue 602, 608 and is received by a photodiode 604, 614 either through transmission or reflection off a structure, such as bone 610. The acquired raw PPG 614 may be modified by or combined with some external motion 616. The modified signal is then sampled to generate a raw signal 618. A preferred sampling rate is 37 seconds at 27.5 Hz to create 1024 data points.

A Fast Fourier transform is performed on the sampled data 620. Using first derivative criteria, bin numbers are identified for all major peaks 622. The identified peaks are then classified as primary and their harmonics 624. Including only a first set of primary and harmonic peaks, the time domain PPG is then reconstructed using the Inverse Fast Fourier transform 626. The second order derivative of the time domain PPG is then calculated 628, revealing a unique Cardiac morphology defined by four systolic waves and one diastolic wave, as previously discussed.

Wave transitions are identified and the height of wave transitions are determined in accordance with a quantitative morphological analysis of the second order derivative of the time domain PPG. A plurality of wave transitions that are taken into consideration include a first wave transition, (a-wave)→(b-wave), a second wave transition, (b-wave)→(c-wave), a third wave transition, (c-wave→d-wave), a fourth wave transition, (d-wave→e-wave), and a fifth wave transition, (e-wave→f-wave), respectively. After the calculation of heights of transitions, they are compared amongst each other for the largest wave transition utilizing a predetermined criterion 630. The criterion for finding the largest wave transition is as follows: Height [(a-wave)→(b-wave)]>{Height[(b-wave)→(c-wave)], Height [(c-wave)→(d-wave)], Height [(d-wave)→(e-wave)], Height [(e-wave)→(f-wave)]}. The above-mentioned criterion for finding the largest wave transition is in no way a limitation and other suitable predetermined criterion may also be employed.

If the criterion is not satisfied, the calculation proceeds to the next point in the second order derivative inverse Fast Fourier Transform 632 and repeats. If the criterion is satisfied, a cardiac pulse morphology or geometry is identified 634 and the number of such cardiac pulse geometries are counted 636 over the sample period, such as 37 seconds, to generate a score.

This process, starting from the reconstruction of the time domain PPG 626 through to the generation of a score 636, is repeated for each primary/harmonic set, thereby yielding a score ($Score_j$) for each primary peak ($P_j$) and corresponding harmonic peaks ($H_j$). Once all of the scores ($Score_j$) are derived, they are compared 638 to each other, i.e. for each primary/harmonic set. The primary/harmonic set with the highest score is classified as the most likely cardiac geometry while the primary/harmonic set with the lowest score is classified as the most likely motion geometry 640.

To perform a double check, correlation coefficients ($C_j$ and $C_k$) for the highest and lowest scores ($Score_j$ and $Score_k$) are calculated 644 by applying a wavelet, such as Symlets #7, Daubechies #9, or Morlet. The sum of the correlation coefficients of each scale over the length of the second order derivative of the inverse Fast Fourier transform is compared 646 to one another. Specifically, $$\text{Rowsum\_}C_j(\text{Scale}) = \Sigma C_j(\text{Scale}, 1 \ldots 1024), \text{ where Scale} = 1 \ldots 30$$

$$\text{Rowsum\_}C_k(\text{Scale}) = \Sigma C_k(\text{Scale}, 1 \ldots 1024), \text{ where Scale} = 1 \ldots 30$$

In a subsequent step 648, a count is performed whereby the number of times $\text{Rowsum\_}C_j > \text{Rowsum\_}C_k$ is counted, yielding $Wscore_j$, and the number of times $\text{Rowsum\_}C_k > \text{Rowsum\_}C_j$ is counted, yielding $Wscore_k$. In step 650, the primary/harmonic set ($P_j, H_j$) with the highest score ($Wscore_j$) is identified as the most likely cardiac geometry while the primary/harmonic set ($P_k, H_k$) with the highest score ($Wscore_k$) is identified as the most likely motion geometry.

The present invention utilizes the novel signal processing method in an oximeter to provide the enhanced detection of physiological signals. One of ordinary skill in the art would appreciate that this signal processing approach could be used in a device that functionally processes physiological signals but is not referred to as an oximeter. Further, as various modifications could be made in the above methods and systems without departing from the scope of the invention, it is intended that all matter contained in the above description should be interpreted as illustrative and not in the limiting sense. For example, other signal acquisition, measurement, and preconditioning systems, or signal transformation, and reconstruction methods could be used while still staying within the scope of the present invention.

What is claimed is:

1. A pulse oximetry system for the determination of a physiological parameter wherein said pulse oximetry system is configured to remove motion artifacts from physiological signals, comprising: an optical sensor for providing said pulse oximetry system with photo-plethysmographic data, wherein said sensor comprises a light emitting diode for emitting light and a photo-detector for detecting said light, wherein said detected light contains information on the photo-plethysmographic data; a processor for processing the photo-plethysmographic data; and a memory unit, wherein said memory unit is operably coupled to said processor, and wherein said processor is configured to: (a) acquire said photo-plethysmographic data; (b) transform the photo-plethysmographic data into frequency domain data; (c) analyze the frequency domain data; (d) reconstruct a time domain data photo-plethysmographic signal from said frequency domain data; (e) analyze a second order derivative of the time domain photo-plethysmographic signal to identify parameters; (f) use said parameters to separate a physiological signal from a motion artifact in the time domain photo-plethysmographic signal; and (g) compute a physiological parameter from said motion artifact independent physiological signal.

2. The system of claim 1 wherein the processor is configured to condition the photo-plethysmographic data prior to transforming the data into the frequency domain.

3. The system of claim 2 wherein conditioning said photo-plethysmographic data reduces spectral leakage from subsequent signal processing and frequency analysis.

4. The system of claim 1 wherein the processor is configured to analyze the frequency domain data to locate candidate spectral peaks before transforming said frequency domain data into time domain photo-plethysmographic signal data, wherein analyzing said transformed data to locate candidate spectral peaks comprises the steps of assigning a largest power amplitude from said data as a primary candidate spectral peak and assigning a next largest power amplitude that is not a harmonic of said primary candidate spectral peak as a secondary candidate spectral peak.

5. The system of claim 1 wherein the processor is configured to analyze the frequency domain data to locate candidate spectral peaks before transforming said frequency domain data into time domain photo-plethysmographic signal data, wherein said analyzing transformed data to locate candidate spectral peaks is performed using a first derivative criteria, wherein said candidate spectral peak is a frequency bin having a slope value equal to approximately zero.

6. The system of claim 1 wherein the processor is configured to compute a second order derivative of the time domain photo-plethysmographic signal after reconstructing the time domain data photo-plethysmographic signal.

7. The system of claim 6 wherein the second order derivative photo-plethysmographic signal is analyzed to determine the absence or presence of cardiac physiologic signal characteristics.

8. The system of claim 7 wherein analyzing said second order derivative photo-plethysmographic signal comprises the step of performing a morphological analysis of the second order derivative photo-plethysmographic signal to determine a unique cardiac morphology, wherein said cardiac morphology consists of a plurality of systolic and a plurality of diastolic waves, and wherein said analysis accounts for a plurality of wave transitions.

9. The system of claim 8 wherein analyzing said second order derivative photo-plethysmographic signal further comprises the step of performing a morphological analysis of the second order derivative photo-plethysmographic signal to determine at least one height of said wave transitions.

10. The system of claim 6 wherein analyzing said second order derivative photo-plethysmographic signal comprises the steps of: determining a plurality of wave transitions, calculating a plurality of heights of said wave transitions, and applying a criterion for detecting a predefined type of wave transition.

11. The system of claim 10 wherein the criterion for detecting a predefined type of wave transition among a first wave, a second wave, a third wave, a fourth wave, and a fifth wave comprises identifying the largest transition between a first wave and a second wave and determining whether a set of first, second, third, fourth, and fifth waves adhere to a formula.

12. The system of claim 1 wherein the time domain photo-plethysmographic data is reconstructed by including only a plurality of primary candidate spectral peaks and a plurality of corresponding harmonic spectral peaks.

13. The system of claim 1 wherein using said parameters to separate a physiological signal from a motion artifact comprises removing motion artifacts from the photo-plethysmographic signal by classifying a first primary-harmonic set with a first highest score as a likely cardiac geometry and classifying a second primary-harmonic set with a highest score as a likely motion geometry.

14. A pulse oximetry system for the determination of a physiological parameter wherein said pulse oximetry system is configured to remove motion artifacts from physiological signals, comprising: an optical sensor for providing said pulse oximetry system with photo-plethysmographic data, wherein said sensor comprises a light emitting diode for emitting light and a photo-detector for detecting said light, wherein said detected light contains information on the photo-plethysmographic data; a processor for processing the photo-plethysmographic data; and a memory unit, wherein said memory unit is operably coupled to said processor, and wherein said processor is configured to: (a) analyze frequency domain data derived from said photo-plethysmographic data, (b) transform the frequency domain data into a time domain photo-plethysmographic signal; (c) analyze a second order derivative of the time domain photo-plethysmographic signal to identify parameters; and (d) use the identified parameters to separate a physiological signal from a motion artifact in the time domain photo-plethysmographic signal.

* * * * *